United States Patent [19]
Morozov

[11] Patent Number: 5,952,191
[45] Date of Patent: Sep. 14, 1999

[54] METHOD OF GROWING SEVERAL SAMPLES OF MICROORGANISMS ON A SINGLE FLAT SURFACE OF SOLID GROWTH MEDIUM

[76] Inventor: Alexei M. Morozov, 1935 Eastchester Rd., Apt. 17D, Bronx, N.Y. 10461

[21] Appl. No.: 08/942,167

[22] Filed: Oct. 1, 1997

[51] Int. Cl.$^6$ ..................................................... C12Q 1/24
[52] U.S. Cl. .......................................... 435/30; 435/288.4
[58] Field of Search ................................. 435/30, 34, 39, 435/288.4, 305.2, 309.1; 422/101, 102

[56] References Cited

U.S. PATENT DOCUMENTS

| | | | |
|---|---|---|---|
| 3,677,904 | 7/1972 | Fitzgerald | 195/103.5 |
| 3,715,280 | 2/1973 | Farmer | 195/103.5 |
| 3,769,936 | 11/1973 | Swanson | 119/15 |
| 3,796,638 | 3/1974 | Guigan | 195/127 |
| 3,912,596 | 10/1975 | Hague et al. | 195/127 |
| 4,042,463 | 8/1977 | Haque | 195/120 |
| 4,053,362 | 10/1977 | Sforza | 195/103.5 |
| 4,072,578 | 2/1978 | Cady . | |
| 4,988,302 | 1/1991 | Smith et al. | 435/298 |
| 5,262,326 | 11/1993 | Jaeger | 435/300 |
| 5,358,871 | 10/1994 | Stevens | 435/204 |

OTHER PUBLICATIONS

MacFaddin, J. Media for Isolation, Cultivation, Identification, Maintenance of Medical Bacteria, Williams & Wilkins, Baltimore, 1985.

Poppe C. Evaluation of Immunomagnetic Separation in Combination with Modified Semi–Solid Rappaport Vassiliadis Medium and Rambach Agar for the Isolation of Salmonella, J of Microbiological Methods 25 237–244 1996.

Senthuran A. Lactic Acid Fermentation in a Recycle Batch Reactor Using Immobilized Lactobacillus casei, Biotechnology and Bioengineering 55(6) 841–853, Sep. 27, 1997.

*Primary Examiner*—Ralph Gitomer

[57] ABSTRACT

A method and apparatus for growth and analysis of microbiological clones. A divider (6) is introduced into a layer of solid growth medium, separating the open surface of the medium into compartments. Appropriately diluted microbiological samples containing known strains of bacteria, yeast or virus infected bacteria are spread around the surface of the compartments. Glass beads can be used for spreading. Means for collecting beads contained within multiple compartments are provided. The divider is removed; means for preserving the structural integrity of the solid medium layer upon removal of the divider are provided. Colonies (in case of bacteria) or viral plaques (in case of virus infected bacteria) are allowed to form and subjected to further analyzes such as replica-plating or membrane lifts, which can now be performed on several samples simultaneously.

8 Claims, 13 Drawing Sheets

6

METHOD OF GROWING SEVERAL SAMPLES OF MICROORGANISMS ON A SINGLE FLAT SURFACE OF SOLID GROWTH MEDIUM

BACKGROUND—FIELD OF INVENTION

This invention relates to growth of microbiological organisms on solid medium. More particularly, it relates to an improved growth container that allows several samples to be grown and analyzed simultaneously.

BACKGROUND—DESCRIPTION OF PRIOR ART

Cloning in microbiological context is a process whereby one cell gives rise to a multitude of genetically identical cells. A suspension of cells is applied onto the surface of solid growth medium; as each cell divides, its progeny stay in close proximity and eventually form a group of genetically identical cells referred to as a colony.

Cloning is used in every modern biological laboratory, most commonly to isolate plasmid vectors (artificially constructed bacterial chromosomes), a crucial step in recombinant DNA technology. Cloning is also indispensable in any work involving microbiological organisms such as bacteria and yeast. In addition, cloning can be performed on viruses. In the latter case, a continuous lawn of bacteria is used; viral clones form plaques, or regions where a progeny of a single virus have multiplied, infected and killed bacteria. Further description will be limited to bacterial work, although the present invention is equally applicable to work with viruses.

Regardless of the microbiological organism or application, cloning always involves applying a suspension of cells onto solid growth medium; allowing each cell to grow and become a colony; finally, analyzing the colonies. Several types of analyses can then be performed. First, each colony can be "picked" from the plate, regrown in liquid medium and subjected to further assays. Second, the colonies can be lifted off the plate onto a membrane, such as a nitrocellulose membrane. The membrane can then be analyzed in several ways including staining and other assays. Third, the colonies can be regrown on a different solid medium by a process known as replica-plating. The surface of solid medium with grown colonies in a plate is lightly pressed against a sterile piece of velvet wrapped around a cylindrical-shaped device called a replicator which matches the geometry of the plate. The velvet-replicator assembly is then pressed against the fresh solid medium surface of another plate. A few cells transferred from each colony are sufficient to form its replica-colony on new medium, if this new medium can support their growth. Replica-plating is thus used to study nutritional requirements of cells in each colony.

Successful cloning requires uniform distribution of cells, and thus colonies, on the surface of medium. If the cells are unevenly distributed, many will be too close and resulting colonies will come in contact, preventing their isolation.

A conventional way of spreading cell suspension on solid medium is by using a glass spreader (See FIG. 1). After the addition of cell suspension 1, spreader 2 is kept stationary at the surface of solid medium 3 while plate 4 is rotated as indicated by the arrows. To adapt to this method, the most commonly used containers for solid medium, or plates, are round, and are known as Petri plates.

Another technique of spreading cell suspension involves glass beads (FIG. 2). Either before or after the addition of cell suspension 1, several sterile beads 5 are added to plate 4 containing solid medium 3. The plate is then shaken gently by hand. The beads are then discarded by inverting the plate.

The latter technique greatly enhances uniformity of spreading by virtue of random motion of the beads, and makes it possible to use plates of any shape.

The idea of using a ball to spread bacterial cultures on solid medium is described in U.S. Pat. 3,677,904 to Fitzgerald, 1972.

When several different cell suspensions are to be plated, a separate plate is used for each sample, greatly complicating the experimental procedure for the following reasons. First, each plate has to be handled individually when pouring melted solid medium for subsequent solidification, when spreading cell suspensions, and when performing analyses such as replica-plating and membrane lifts. Thus, the more plates there are, the longer each step takes. For instance, replica-plating might take 5 minutes if there is only one plate; if there are 25 plates, it might take 125 minutes, or over two hours. Second, the plates are hard to carry. It is impossible for one person to carry more than about 20 plates at a time. If a tray is used to carry several stacks of plates, one has to be extremely careful to prevent the stacks from collapsing. If a plate with an experimental sample falls on the floor, the sample is very likely to get contaminated. Third, experimental conditions within each plate usually are not identical. For example, thickness of the medium layer, the time a membrane is left on a plate when performing membrane lifts, conditions the membranes are subjected to, or the pressure applied when performing replica-plating, can vary from plate to plate. Fourth, sometimes only a fraction of the plate's area would suffice for each sample, in instances when one is studying properties of a genetically identical cell culture and therefore large numbers of colonies are not required. If, for example, 25 samples are to be analyzed, and only one fifth of the plate's area is sufficient for each, but one plate is still used for each sample, then 20 extra plates are unnecessarily spent. The plates are subsequently classified as biohazard waste and the plastic or glass they are composed of is not recycled. Small Petri plates are commercially available, but they are inconvenient to handle (e.g. when pouring medium), and they cannot be stacked as high as bigger Petri plates. It is also inconvenient to have more than one replicator device and more than one size of membranes to be used with different size Petri plates. Consequently, only one size of Petri plates, 10 cm diameter, is predominantly used.

One can see that there is a need for a method to grow and analyze several samples on one plate. One existing solution is a compartmentalized plate, which is identical to a Petri plate, except it has a divider permanently attached to the bottom and walls of the plate. The divider separates the plate into sectors. Melted solid growth medium can be poured into each compartment and allowed to solidify. Cell suspension can then be added to each compartment, and spread using glass beads. However, compartmentalized plates offer the following disadvantages. First, the dividers greatly complicate membrane lifts and replica-plating analyses on the compartmentalized plates. Second, medium has to be poured separately into each compartment, which is time-consuming and usually results in unequal thickness of the solid medium layer in different compartments. Third, removing beads from a compartmentalized plate by inverting it is cumbersome. Because of the above disadvantages, compartmentalized plates are not usually used in cloning.

A technique that involves the insertion of a divider into solid medium is described in U.S. Pat. No. 3,715,280, to Farmer, 1970 ("Farmer patent"). However, the intended use of the test assembly disclosed in the Farmer patent is not cloning, but rather characterization of biochemical properties of unknown strains of microorganisms (column 1, line 1–26; column 4, line 15). It is meant to replace not a multitude of Petri plates or similar plates, but a multitude of test tubes (column 1, line 18–20). Recombinant DNA technology, which has made cloning such a widely used technique, was at a very early stage of development when the Farmer patent was issued.

The following illustrates some of the differences between the use proposed in the Farmer patent, namely, characterization of biochemical properties of unknown strains of microorganisms, and the use for cloning.

For the purposes of characterization of biochemical properties of unknown strains of microorganisms, growth and analysis of individual clones (colonies in case of bacteria or yeast, plaques in case of viruses on a bacterial lawn) is not performed. Rather, the strain under study is inoculated onto a growth medium, and the absence or presence of growth is noted. On the other hand, for the purposes of cloning, the samples need to be sufficiently diluted and evenly distributed around the surface of growth medium to ensure spatial separation of the clones; the test areas need to be sufficiently large to accommodate a certain number of well-separated clones.

For the purposes of characterization of biochemical properties of unknown strains of microorganisms, it is important to provide maximal isolation of individual test areas enclosed by the bottom of the growth container and the vertical walls of the divider, due to the presence of swarming bacteria in some samples. U.S. Pat. No. 4,053,362 to Sforza (1976) is a modification of the Farmer patent wherein more efficient isolation of individual test areas is provided. On the other hand, for the purposes of cloning, a vertical divider at the surface of the growth medium is sufficient to isolate the test areas, since microorganisms used for cloning are immobile when grown on solid growth medium. After the samples are spread within the individual test areas enclosed by the divider, the divider can be removed.

Thus, the geometrical requirements and the mode of operation of a test assembly used for cloning are entirely different from those of a test assembly used for characterization of unknown strains of microorganisms.

As a consequence of its different use, the device described as the Preferred embodiment in the Farmer patent cannot be used for cloning for the following reasons. First, if glass beads were used to spread microbiological samples within the compartments, there is a possibility of the beads spilling over into neighboring compartments, thus cross-contaminating the samples when the assembly is inverted to discard the beads. Second, the divider described as a part of the Preferred Embodiment in the Farmer patent has such dimensions that prevent its removal without disturbing the structural integrity of the solid medium. Indeed, if the area of contact between the solid medium and the divider exceeds that between the medium and the bottom of the plate, the medium will adhere to the divider when its removal is attempted. The area of contact between the bottom of the plate and the solid medium piece enclosed within each compartment, as described in the Farmer patent (column 2, line 63), is equal to the area of the plate (160 mm squared equals 25,600 $mm^2$) divided by the number of compartments (49), 522.4 $mm^2$. The divider is described to be tightly fitted into the plate (column 1, line 63); therefore, the area of contact between the segment of solid medium and the divider equals the thickness of medium layer (7 mm) multiplied by the perimeter of a compartment (23 mm times 4 equals 92), 644.0 $mm^2$. Thus, the area of contact, and consequently the force of adhesion, between the medium and the divider exceeds that between the medium and the plate. If removal of the divider is attempted, the medium will separate from the plate and will also be removed. Thus, for the purposes of performing replica-plating, membrane lifts or similar analyzes, the divider described in the farmer patent is essentially not removable.

The unsuitability of the device described in the Preferred embodiment in the Farmer patent for use in cloning further illustrates its different intended use.

Objects and Advantages

Accordingly, the object of my invention is to provide a means of growing and analyzing several samples on one Petri plate simultaneously, thus offering the following advantages over the prior art:

1. Much faster to use than the corresponding number of individual Petri plates; time savings of a hundred-fold or more for individual experimental steps. For example, pouring the plate, spreading, replica-plating and membrane lifts can be performed in one step each, in a matter of minutes. Therefore, if a hundred samples are plated on one plate, a hundred-fold reduction in operation time is achieved. Adding cell suspensions can be a matter of minutes, too, especially if a multipipetter is used.

2. Greater number of samples can be used at a time than presently possible. It is presently impossible to handle more than thirty or forty Petri plates at a time. For example,. a nitrocellulose filter might need to be applied to the surface of the plate and removed in no more than five minutes according to an experimental protocol. Placing filters on forty plates, however, takes much longer than five minutes. Thus, by the time one is finished placing the last filter, the first filter is already well past its time to be removed. The present invention allows one to use a single filter for any number of samples, eliminating the timing constraints, so that great numbers of samples can be handled simultaneously.

3. Easy to manufacture: can be made of plastic, glass, disposable or autoclavable material. In the simplest embodiment, a single mold is required.

4. Convenient to handle: minimizes stacking.

5. More compact: saves space and material. Ten trays with a hundred samples in each can fit on a shelf in a refrigerator; a thousand individual Petri plates can take up the entire cold room.

6. More orderly. Each Petri plate has to be individually labeled. It is considered good practice to put the date, the name of the investigator, and the name of the sample on each plate. A plate containing a hundred samples is much easier to label, since much of the information has to be written only once. In addition, trying to find one sample out of a thousand is much more convenient when one has ten plates with a hundred samples in each, each sample labeled on the cover, than if one has a cold room filled with a thousand Petri plates.

7. Consistency of experimental conditions. All samples contained within a tray are subjected to identical experimental conditions, which is not the case when individual Petri dishes are used. For instance, thickness of the layer of growth medium, pressure applied to the replicator, or the processing of membranes can vary considerably.

More specifically, the object of the present invention is to adapt the divider described in the Farmer patent for use in cloning by:
1. Providing means for preserving the structural integrity of the agar when the divider is removed.
2. Providing means for collecting the beads and preventing cross-contamination of samples within the compartments.

BRIEF DESCRIPTION OF THE DRAWING

In the drawings, closely related figures have the same number but different alphabetic suffixes.

Figure 1:
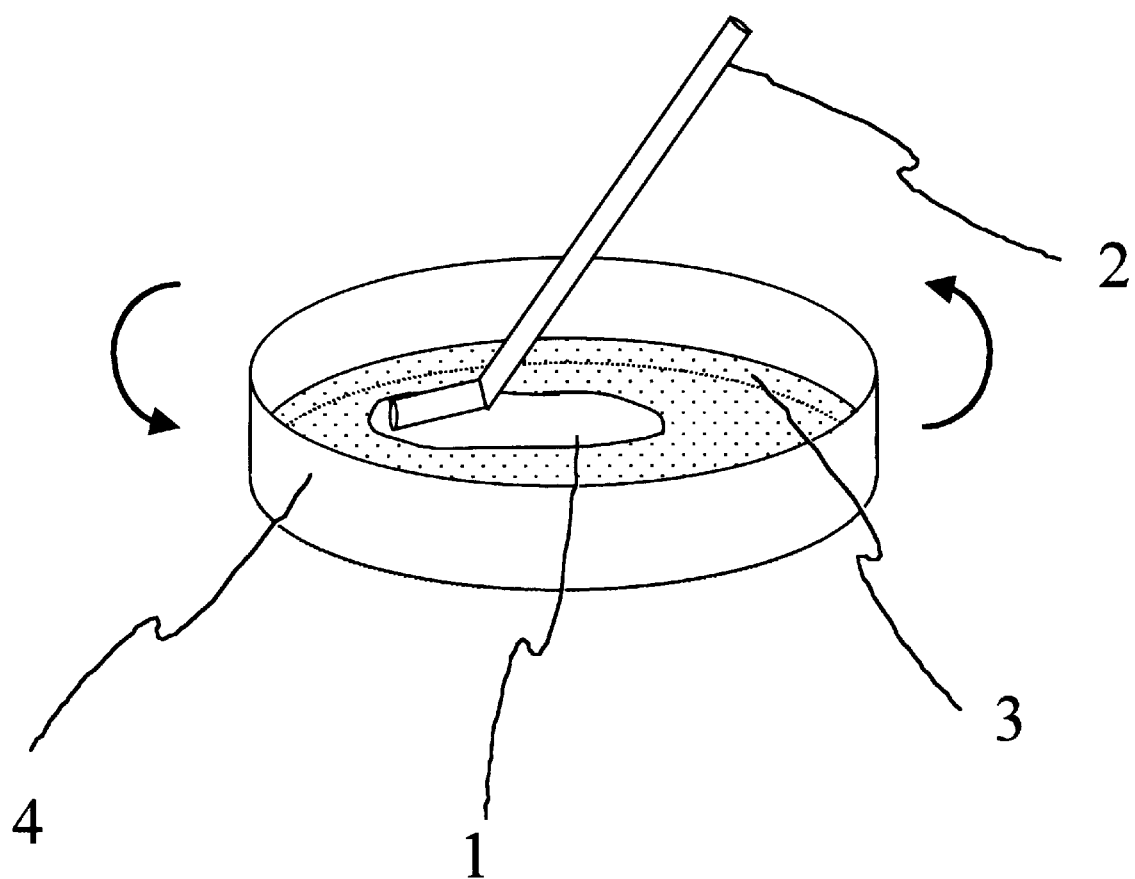
FIG. 1 shows the use of a glass spreader to spread the microbiological sample on the surface of solid growth medium contained within a Petri plate.
Figure 2:
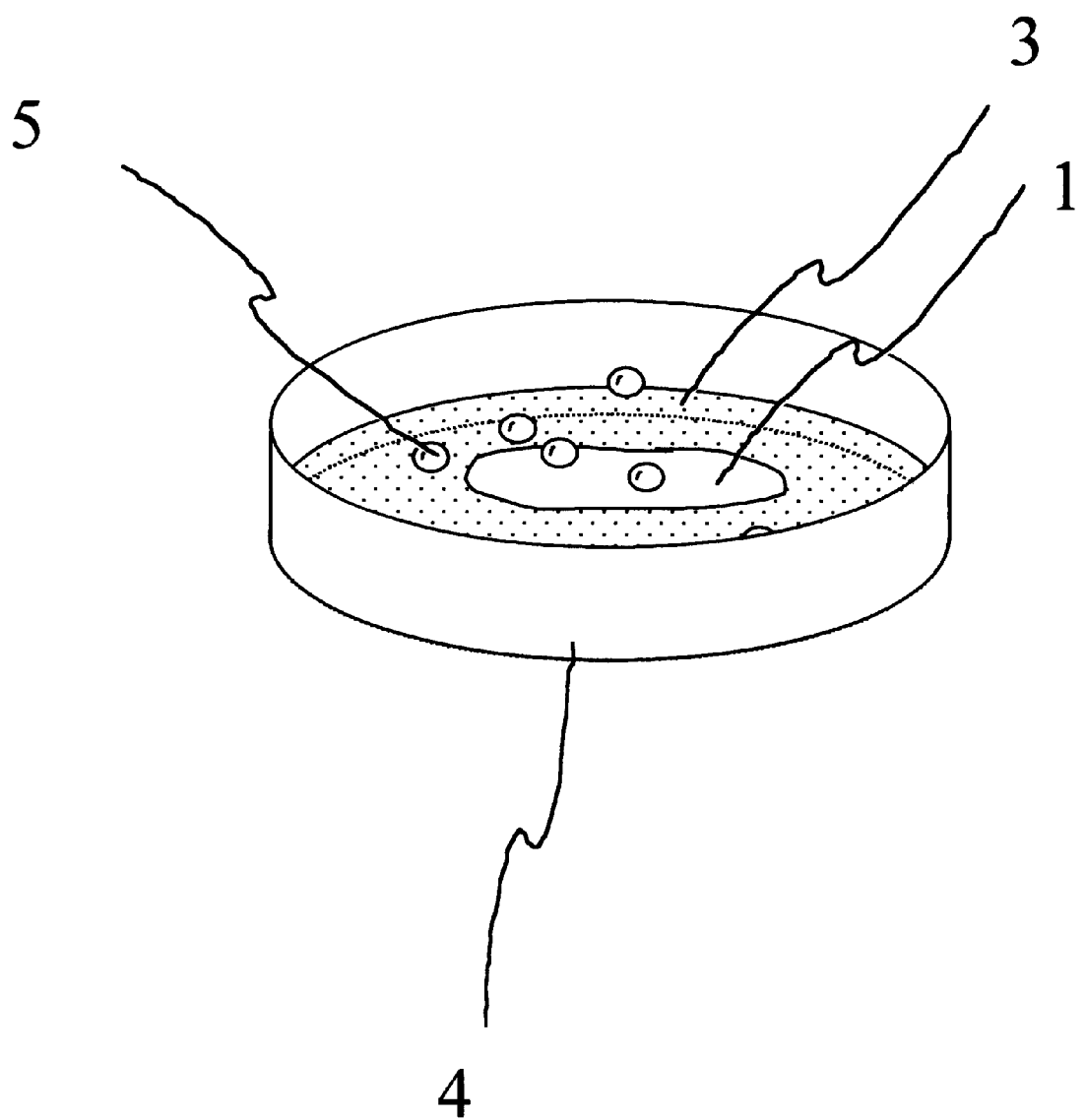
FIG. 2 shows the use of glass beads to spread the microbiological sample on the surface of solid growth medium contained within a Petri plate.

REFERENCE NUMERALS IN DRAWING 1 cell suspension
2 spreader
3 solid growth medium
4 plate
5 beads
6 divider
7 compartment
8 closure
9 hole in closure
10 legs on divider
11 supports on plate
12 collecting cover
13 overhang on collecting cover
14 seal on closure
15 seal on underside of divider
Description of Invention The present invention describes a device that allows one to plate cell suspensions, and then grow and analyze colonies of several samples on one plate, instead of using a separate Petri plate or similar plate for each sample.

Figure 3:
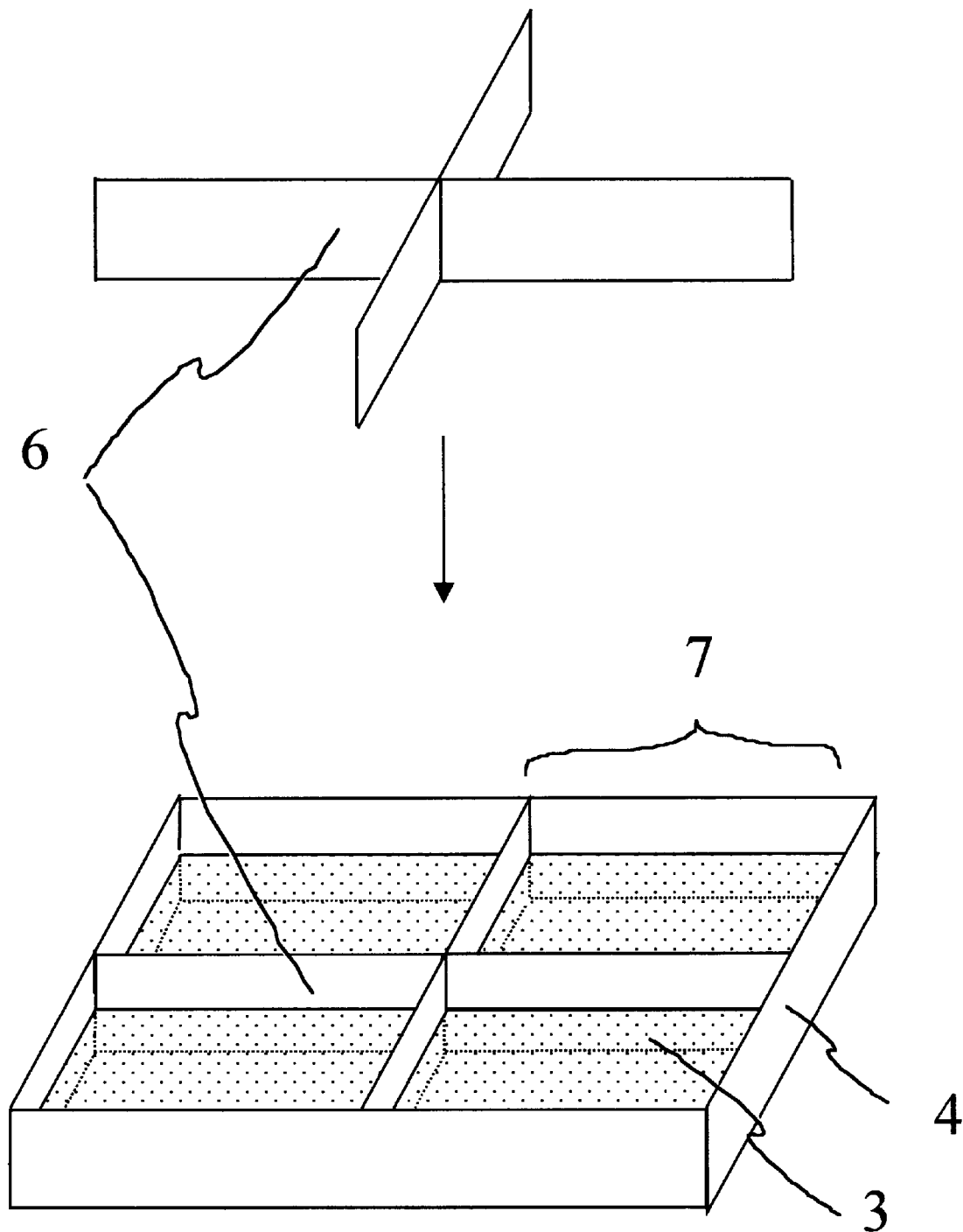
FIG. 3 shows a divider that can be inserted into a Petri plate.

Specifically, as shown on FIG. 3, a divider 6 is suggested that is inserted into growth medium 3 to divide the surface of the medium into compartments 7. Cell suspension is then added to each compartment, followed by the addition of glass beads. The plate is then shaken, causing the beads within each compartment to spread the suspension on the surface of the medium. The beads is then discarded. The divider is then removed.

Figure 4A:
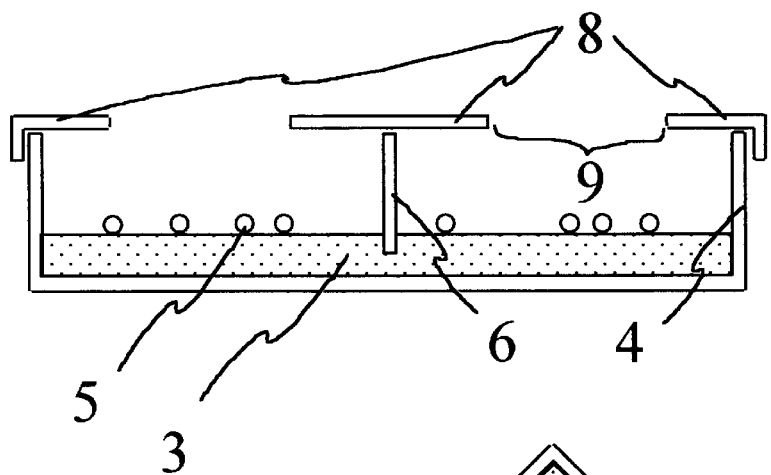
FIGS. 4A, 4B and 4C show a plate in cross-section with an inserted divider, demonstrating the use of a cover with holes to prevent spilling of beads into neighboring compartments when the plate is turned to collect the beads.
Figure 4B:
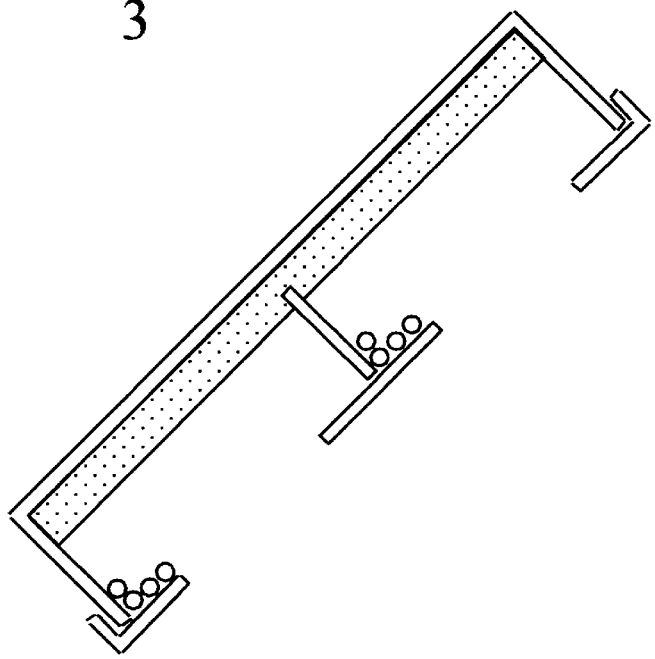
Figure 4C:
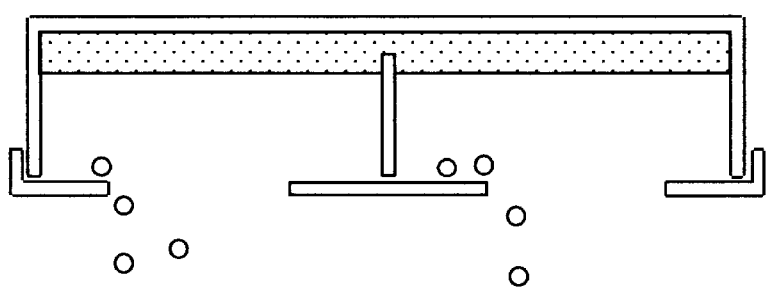
Figure 9:
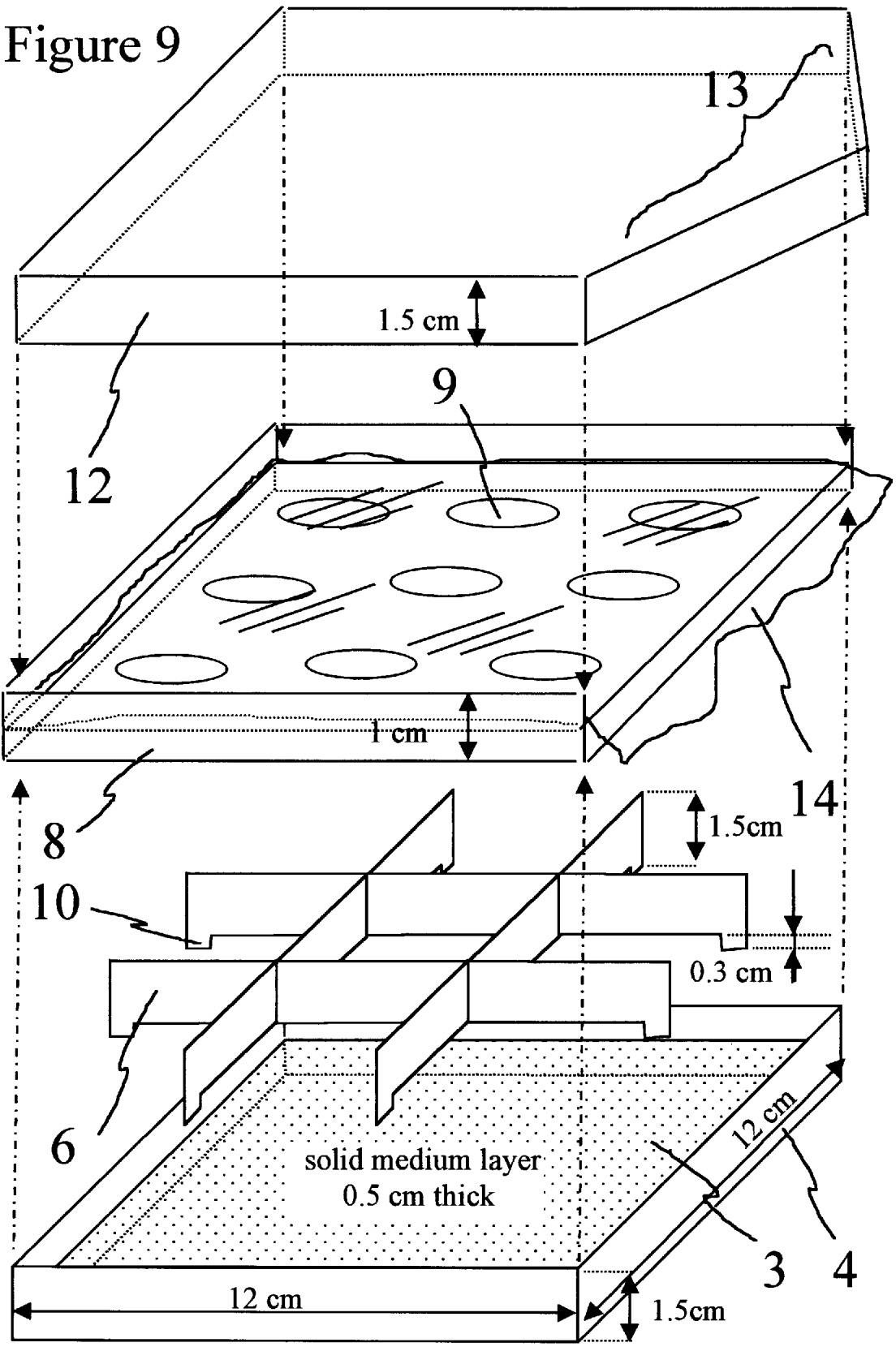
FIG. 9 shows a preferred embodiment of the invention

To prevent the beads from getting from one compartment to the other as the plate is being turned, thus causing cross-contamination of samples, an assembly consisting of a closure and a collecting cover is suggested, as shown on FIG. 9. A closure 8 has a hole above each compartment 7. FIG. 4A shows a cross-section of plate 4 with an inserted divider 6, showing the medium layer 3, beads 5, and closure 8 with its holes 9. When such a cover is placed on plate 4 containing a divider, the beads can only leave their compartment through hole 9. The holes have to be sufficiently small as compared to the area of compartment 7 in order to prevent beads from passing through the hole, as shown on FIG. 4B, until the plate is turned upside-down completely. When the plate is finally completely upside down, as shown on FIG. 4C, the beads leave their compartment; however, at this point it is impossible for the beads to enter any other compartment because it is now above them. To facilitate collection of beads, a second cover is suggested, as described below.

Several key features of the divider are essential for successful implementation of the above technique. First, the walls of the divider must extend upwards above the level of the surface of solid medium high enough to effectively confine the beads within compartments despite vigorous shaking. Second, the geometry of the divider must be such that the divider can be removed without affecting the structural integrity of the medium. More specifically, the horizontal area of the compartment must exceed the area of contact between the solid medium and the divider. This is necessary to ensure that the net force of adhesion between the medium and the bottom of the plate is greater than that between the medium and the divider; otherwise, as the divider is being removed from the plate, the medium will remain attached to the divider and will also be partially or completely removed from the plate. Third, the divider can be made of a material that is less adhesive to solid medium.

Figure 5:
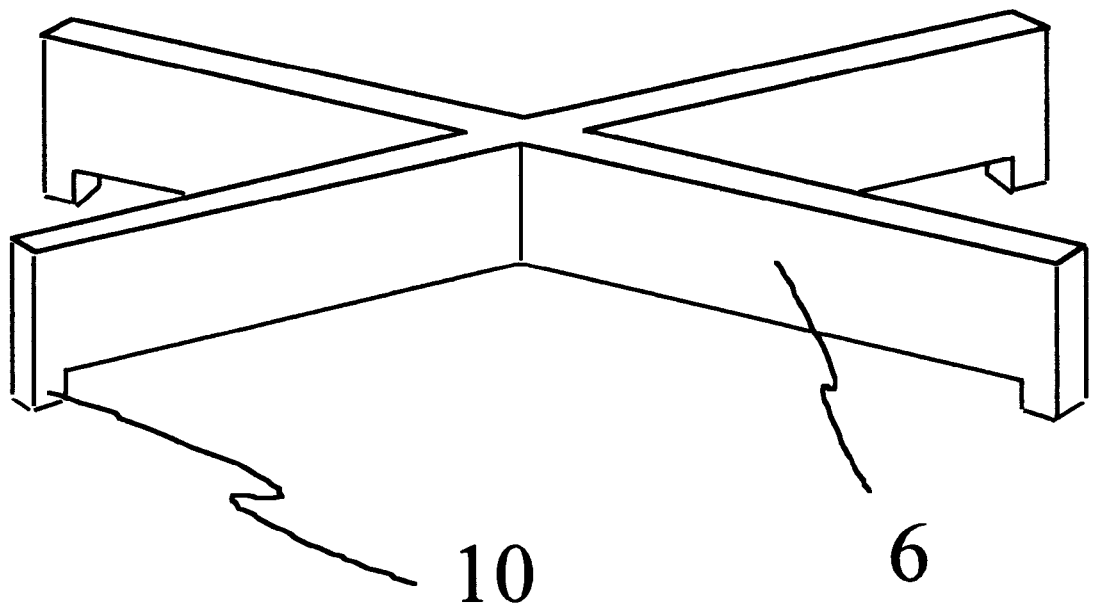
FIG. 5 shows a divider with supports.
Figure 6:
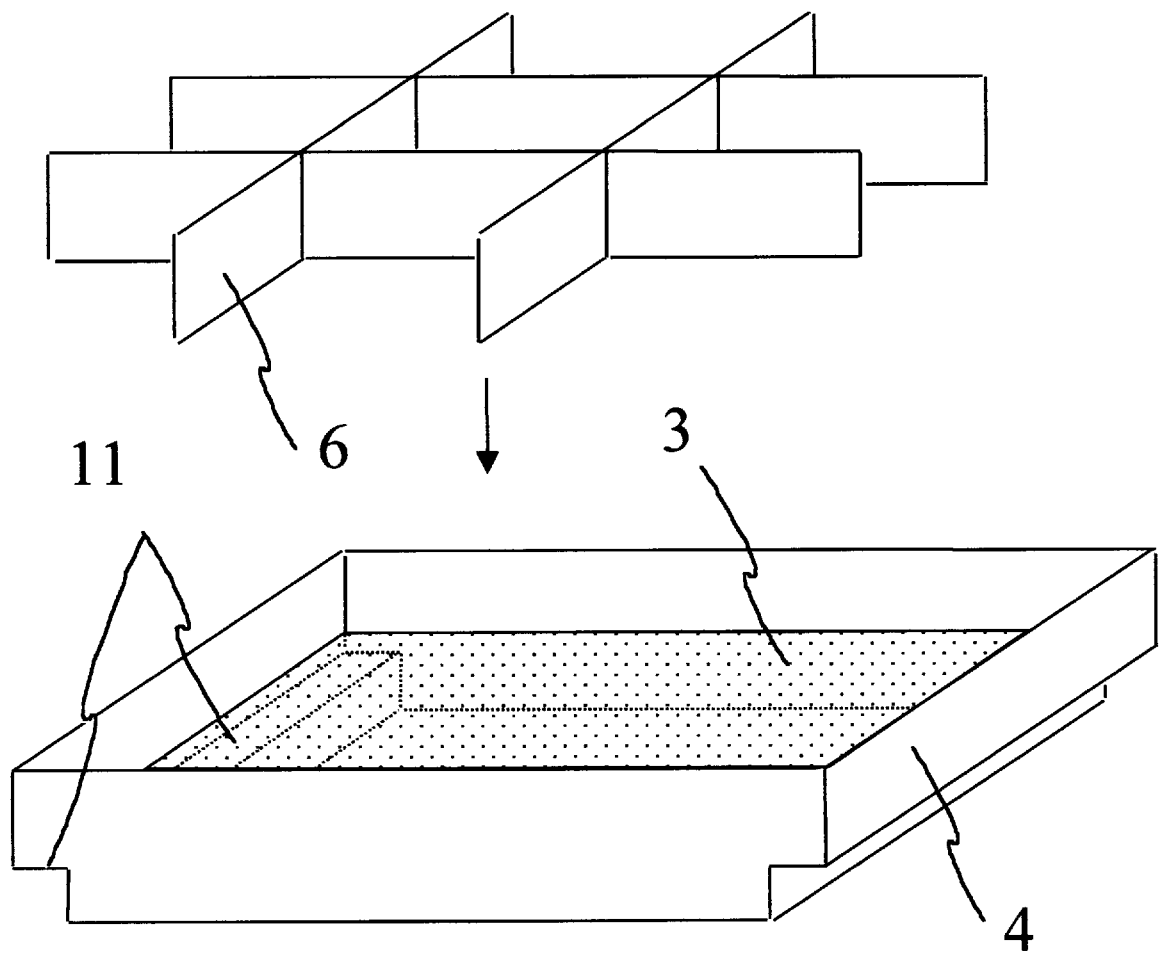
FIG. 6 shows a plate with supports for the divider
Figure 7:
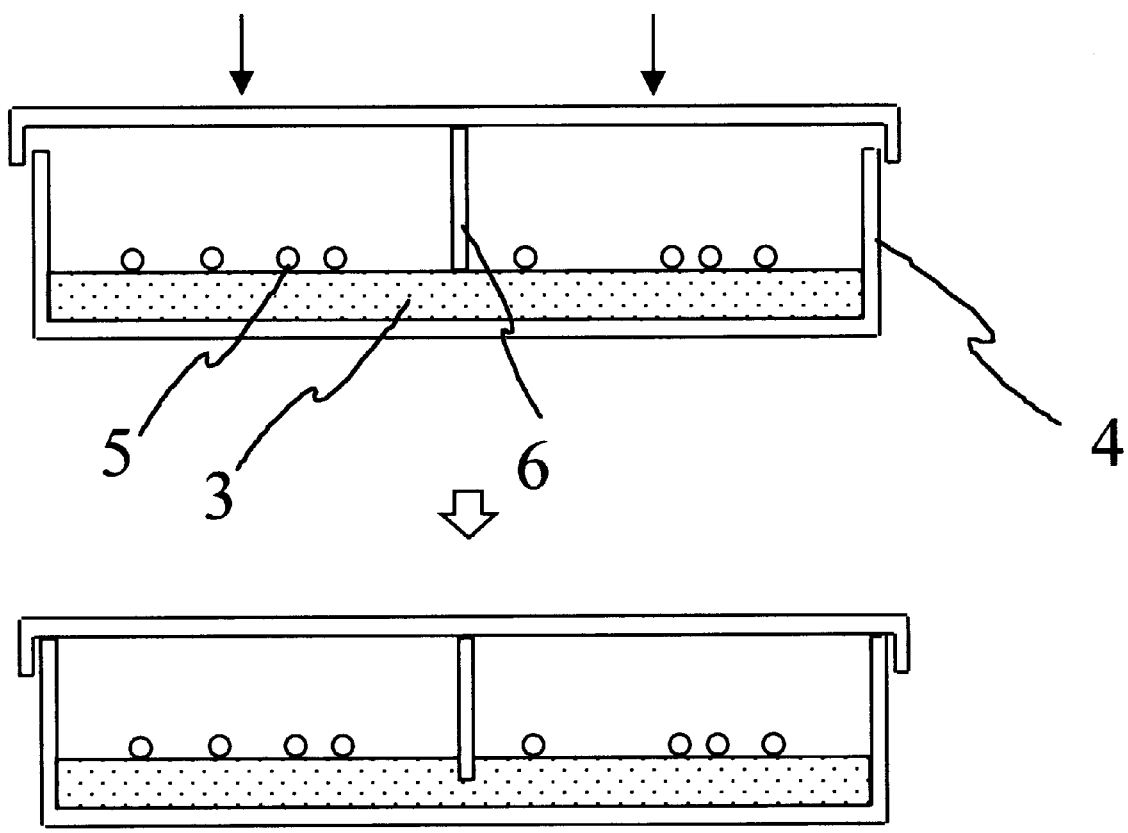
FIG. 7 shows a plate in cross-section with an inserted divider, the latter being pushed the solid medium by applying pressure on a cover.
Figure 8A:
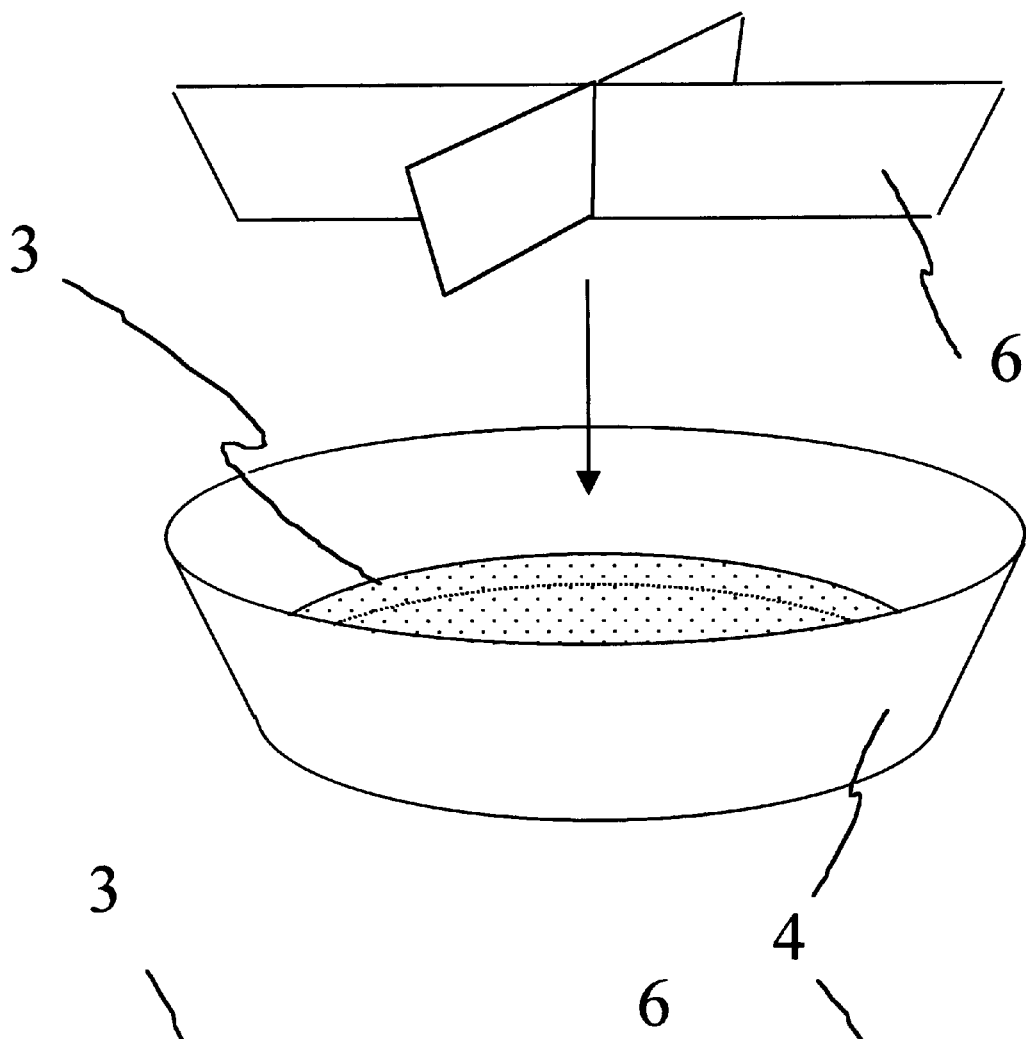
FIGS. 8A and 8B show a plate with the side walls sloping outwards, and a matching divider that is prevented from reaching the bottom of the plate when inserted into it.
Figure 8B:
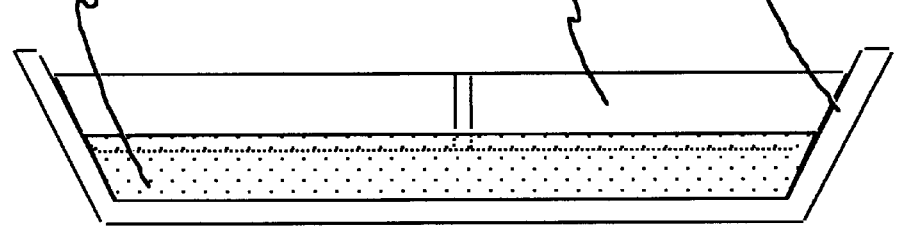

Another way to prevent the divider from disturbing the structural integrity of the solid medium layer as the divider is being removed is to prevent the divider from making full contact with the bottom of the plate; this can be achieved in the following ways. First, the divider can have downwards protrusions or supports 10 as illustrated on FIG. 5, positioned at the lower edge of the divider. Only these supports will make contact with the bottom of the plate, so that the solid medium within each compartment will not be completely separated from solid medium in the neighboring compartments, and so that the area of contact between the divider and the medium is minimized. Second, the plate can have supports 11 that the divider will rest on, as illustrated on FIG. 6, again not allowing full contact of the divider with the bottom of the plate. Third, the divider can be pushed into agar only a fraction of the thickness of the solid medium layer. For instance, as shown in cross-section on FIG. 7, divider 6 can be placed onto the surface of solid medium, with closure 8, or any other cover, placed over it. As the cover is being pushed down, the divider will enter the layer of medium. The vertical extent of the divider can be made such that when the cover is completely closed and rested on the upper edges of plate 4, the divider is inserted into the layer of solid medium 3 by only a fraction of the layer's thickness. This will also allow the divider to be pushed into agar, instead of removing it, subsequent to removal of beads, provided the vertical extent of the divider is less than the thickness of the solid medium layer. Fourth, plate 4 can have its vertical walls sloped outwards at an angle, as shown on FIGS. 8A and 8B, these walls being a section of a cone, not a cylinder. A fitting divider would have its outer edges also sloped at the same angle; if the divider is made from nonflexible material, the diameter of the divider can be made such that the divider cannot reach the bottom of the plate when inserted into it.

Description of the Preferred Embodiment

The preferred embodiment of the present invention is described below and illustrated on FIG. 9 in a disassembled form. Plate 4 is in the shape of a container with rectangular bottom and vertical side walls, containing a layer of solid growth medium 3. Divider 6 is inserted into the medium layer. Divider 6 is a grid-shaped divider consisting of equally spaced parallel vertical uninterrupted walls forming a rectangular grid by intersecting each other at the right angles. When inserted into solid medium layer 3, divider 6 divides the layer into equal rectangular compartments 7. The size of the divider is such that the vertical outer edges of the divider walls make tight contact with the vertical walls of plate 4. Each wall of divider 6 has supports 10 extending downwards directly under the vertical outer edges of the divider walls. Supports 10 rest on the bottom of plate 4. The vertical length of supports 10 is less than the depth of solid medium layer 3. The height of divider 6 is such that when supports 10 are rested on the bottom of plate 4, the top edge of divider 6 is the same height as the upper edge of the plate. In other words, the height of the divider, including the supports, equals the height of the inner surface of the side wall of the plate.

Closure 8 consists of a horizontal surface and side walls extending both upwards and downwards from the outer edge of the horizontal surface. The size of cover 8 is such that the side walls extending downwards from cover 8 fit snugly over the side walls of plate 4, forming a substantially air-tight seal. Horizontal surface of cover 8 has substantially round holes 9 that are spaced in such a way as to be each situated directly above a compartment 7 of divider 6. Holes 9 have to be sufficiently small in comparison to the area of compartments 7 so that when beads are contained in the compartment and the whole assembly is turned over, cover 8 will partially enclose each compartment to prevent the beads from falling out until the whole assembly is turned a complete 180°, as shown on FIGS. 4B and 4C.

Closure 8 has a vertical wall around its edge extending not only downwards towards plate 4, but also upwards towards collecting cover 12. The upwardly extending walls of cover 8 fit snugly over vertical walls of cover 12. The side wall extending upwards is missing on one of the four edges of closure 8 to accommodate overhang 13 of cover 12. Closure 8 is covered with cellophane seal 14.

Collecting cover 12 is a container identical in its dimensions to plate 4, except its horizontal surface at one of its four sides extends further out as compared to plate 4, forming an overhang 13. The vertical side wall of cover 12 follows the entire edge of the horizontal surface of cover 12, including overhang 13, and extends downwards from horizontal surface.

The incubation cover (not shown) is identical to a commonly used Petri plate cover, except it is sized to match plate 4. Like a commonly used Petri plate cover, it does not form an air-tight seal with the plate and thus allows for aeration of the environment within the plate.

Figure 13:
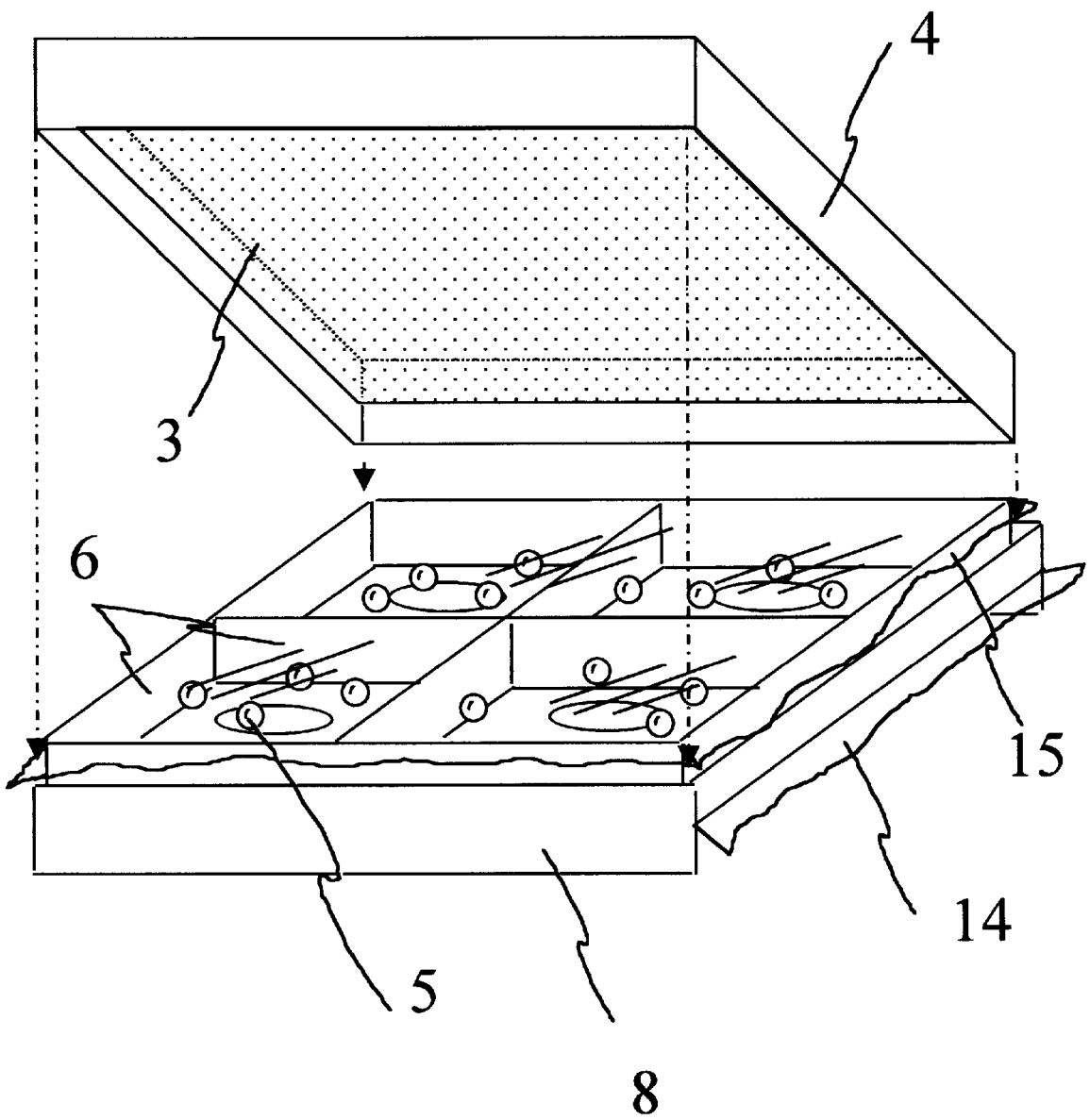
FIG. 13 shows an alternative embodiment of the invention.

Approximate preferred sizes are indicated on FIG. 13.

All of the components described in the present invention, except seals 14 and 15, can be made of any material that is commonly used to make Petri plates, such as polystyrene or glass, or any other suitable material. Seals 14 and 15 can be made of cellophane or any other suitable material.

Operation of the Preferred Embodiment

In a preferred mode of operation, solid growth medium 3 (e.g. agar-based) is melted by autoclaving, poured into plate 4 and allowed to solidify. After medium 3 solidifies, it has to be dried to get rid of excess moisture by removing the cover and keeping the plate at room temperature for thirty minutes. Divider 6 is then inserted into the plate. Sterile beads 5 are then added to each compartment 7. The plate is then covered with the closure 8, which is already covered with cellophane seal 14. The above steps must be performed aseptically and can be performed either by an individual researcher or by the manufacturer. The assembly can then be stored in appropriate conditions (4° C.) until use.

Immediately before use, cellophane seal 14 is removed. Cell suspension is then added into each compartment 7 through the hole 9 with the aid of a pipetter, in a total volume not exceeding 3 microliters per square centimeter of the area of the compartment. After cell suspension has been added to some or all of compartments 7, the assembly is gently shaken, causing beads 5 to roll inside the compartments and spread cell suspension on the surface of medium layer 3. Collecting cover 12 is then placed over closure 8; the resulting assembly is inverted upside down, causing the beads to fall through holes 9 into collecting cover 12. Gentle agitation of the assembly ensures complete collection of beads. The assembly is then slightly tilted so that overhang 13 becomes the lowest point of collecting cover 12, causing all beads to assemble at overhang 13. The assembly is then positioned over a collection container for used beads (not shown) and is tilted further, lowering overhang 13 and raising the wall of cover 12 opposite to overhang 13, until beads fall out from overhang 13. Collecting cover 12 and closure 8 are discarded, or autoclaved and reused (if made from autoclavable material). Divider 6 can then be removed from the plate, either immediately, or at any time prior to performing assays which require the removal of the divider. Plate 4 is covered with incubation cover (not shown; see above) and incubated at the appropriate temperature in an inverted position as conventionally done.

Summary, Ramifications, and Scope

Although the description above contains many specificities, these should not be construed as limiting the scope of the invention but as merely providing illustrations of some of the presently preferred embodiments of this invention.

For example, the divider can consist of a hundred compartments (10 rows of 10 compartments, or 5 rows of 20, or in a similar arrangement), having the same dimensions of each compartment (4 cm by 4 cm) and the same vertical dimensions as in the Preferred Embodiment, thus the plate now being 40 cm by 40 cm in its horizontal dimensions (for the case of 10 rows of 10 compartments), not 12 cm by 12 cm as shown on FIG. 9 for the case of 3 rows of 3 compartments. Other numbers of compartments, for example 4 (e.g. 2 rows of 2 compartments) or 999 (e.g. 33 rows of 33 compartments), may be found convenient.

Figure 10:
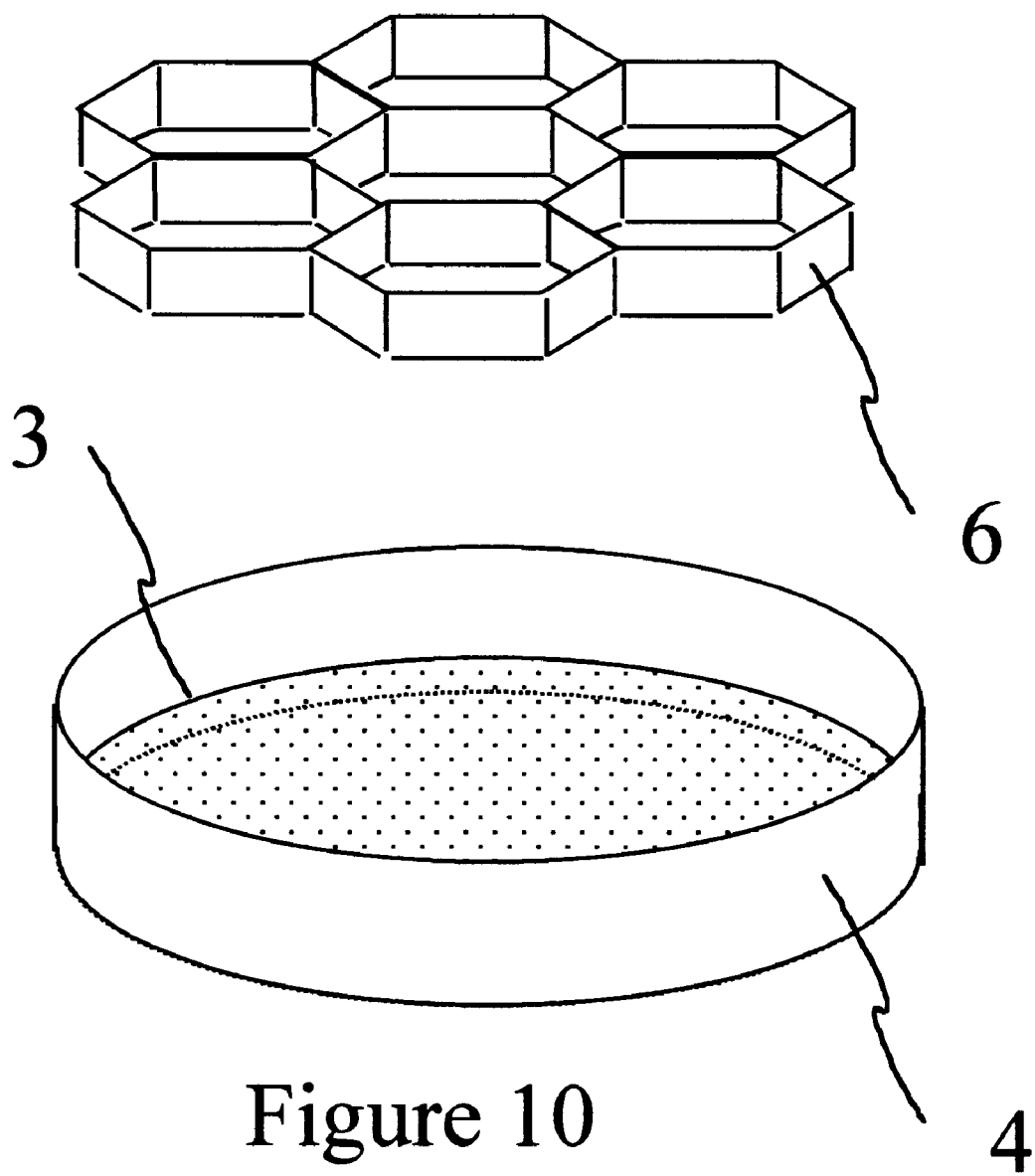
FIG. 10 shows a honeycomb-shaped divider

Divider 6 can be honeycomb-shaped with hexagonal compartments, as shown on FIG. 10.

Divider 6 can be inserted before pouring solid medium 3. Plastic seal 14 can be left in place and punctured by the pipette when adding cell suspensions to the compartments.

Figure 11:
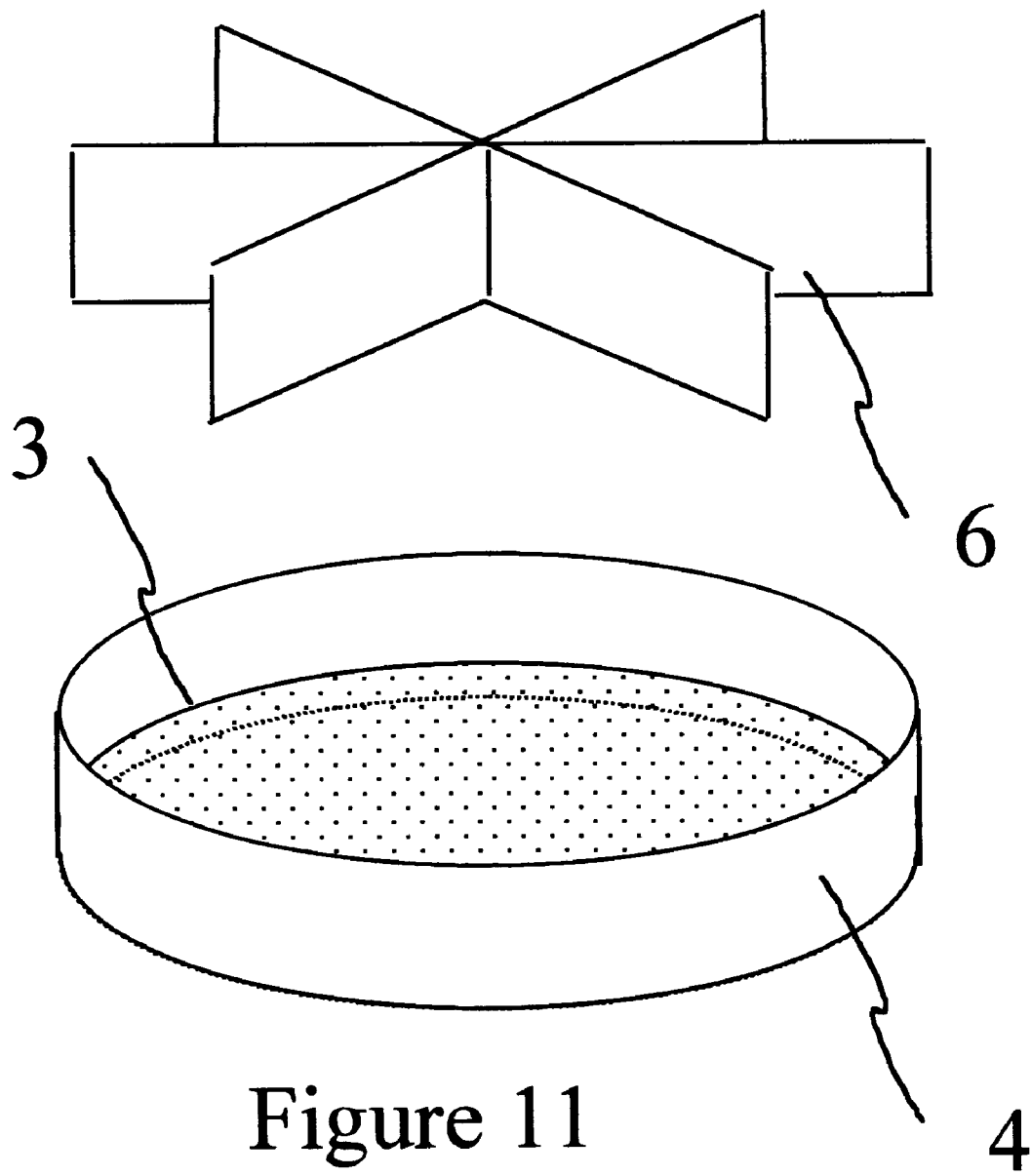
FIG. 11 shows a divider comprising a set of radially extending walls
Figure 12:
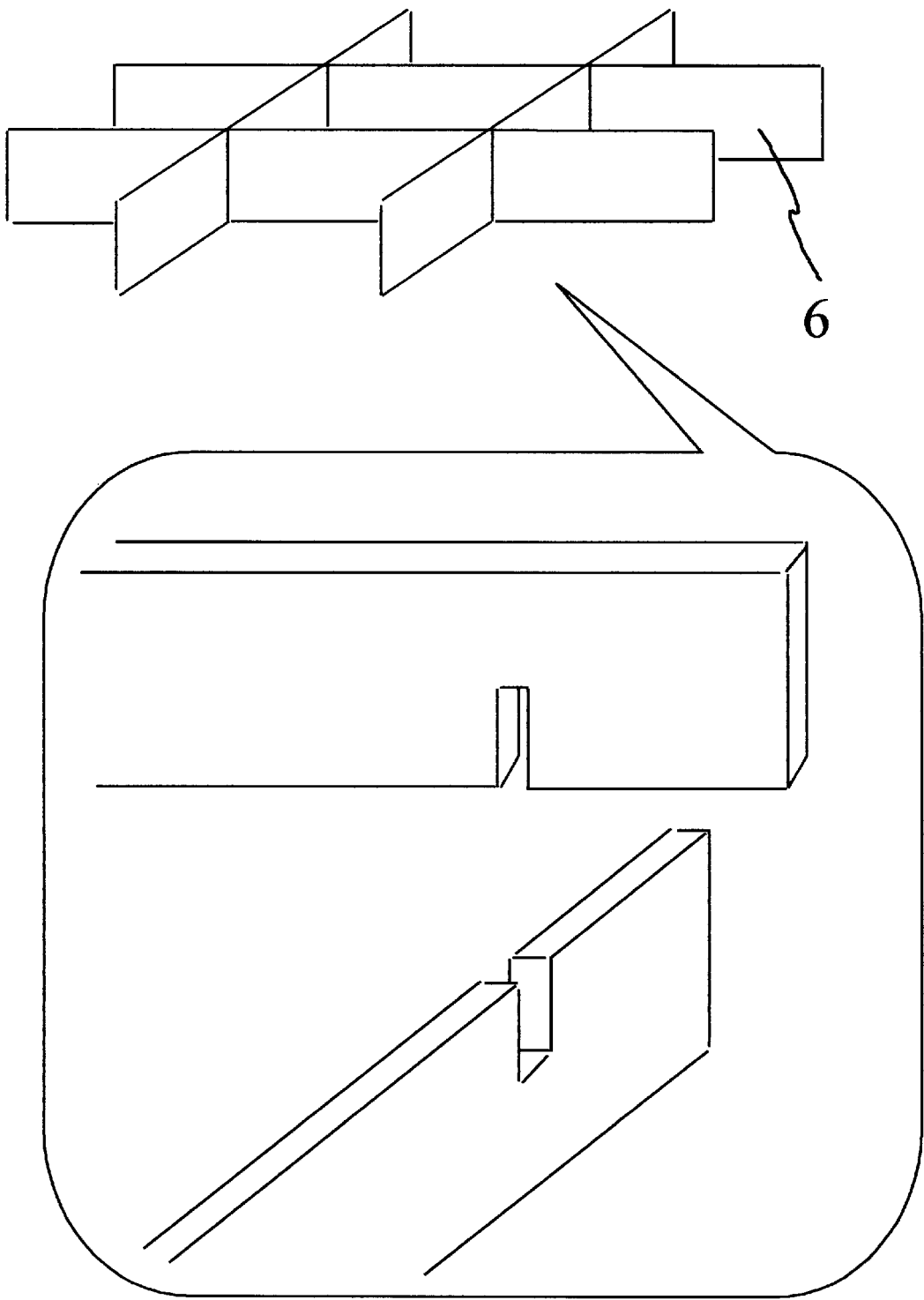
FIG. 12 shows a mode of assembly of a divider

Plate 4 can be round, divider 6 consisting of radially extending walls such as to divide the plate into sectors as shown on FIG. 11; holes 9 in cover 8 would be positioned in a circle.

Divider 6 can be assembled from individual "building blocks," for example as illustrated on FIG. 13, where the walls are shown to have equally spaced slots that are used to interlock the walls at each point of intersection. All walls parallel to each other, e.g. those oriented "left to right," have slots facing upwards; the rest of the walls, i.e. those oriented "back to front," have slots facing downwards. The building blocks can be manually assembled in various ways to generate grid-like dividers with varying numbers and sizes of compartments 7. All slots facing down have to be engaged, otherwise they will act as interconnections between compartments. However, not all slots facing up have to be engaged. For instance, if the assembled divider has the dimensions of divider 6 in the Preferred Embodiment, and only half of slots looking upwards are engaged, in an alternating pattern, then each compartment will be dimensioned 4 cm by 8 cm. If the compartments are large, the number of compartments 7 can exceed the number of holes 9; no change in mode of operation is required.

Divider 6 can be made of flexible material such as sufficiently thin polypropylene so that the sizes of sector-shaped compartments can be manually adjusted before inserting the divider into solid medium. The number of holes in cover 8 can be large to accommodate different relative sizes of the sectors. Alternatively, the divider can have a flexible hinge at the center and nonflexible radially extending walls, as shown on FIG. 11.

Divider 6 can be ring-shaped so that, when inserted into solid growth medium, it divides it into two compartments, one enclosed by the divider and one comprising the rest of the plate.

Divider 6 can be dimensioned such that it can be pushed into medium layer 3 subsequent to the removal of beads. The vertical extent of the divider needs to be such that when it is placed on the surface of medium 3 and pushed into medium 3 by closing and pressing on cover 8 (FIG. 7), the divider is not inserted into medium completely. Supports 10 are then unnecessary. The medium layer has to be thick enough compared to the vertical extent of the divider so that when cover 8 is removed and divider is pushed down by hand, the divider becomes completely embedded inside medium layer 3.

Closure 8 can be permanently attached to divider 6. Supports 10 are then unnecessary. Mode of operation will be unchanged, except the unit consisting of divider 6 attached to cover 8 is inserted first and then beads are added to each compartment through the holes.

As shown on FIG. 13, the unit consisting of divider 6 attached to cover 8 can be inverted upside down, beads added to each compartment, then plate 4 containing medium layer 3 also inverted upside down and placed over said unit (seal 15 is removed) thus inserting the divider into medium and engaging the seal between side walls of cover 8 and side walls of plate 4. The whole assembly is then inverted back into normal position, seal 14 is removed, and cell suspensions are added to each compartment. For the beads to be effectively contained within the peripheral compartments, these compartments have to be bounded by divider walls from all four sides, the same way as the compartments close to the center are. This is shown on FIG. 13 for the case of four compartments, all of which can be considered "peripheral." Thus, divider 6 on FIG. 13 contains four extra walls compared to divider 6 on FIG. 5. When such a divider as that on FIG. 13 is inserted into plate 4, the outer walls of the divider will be opposed to the walls of the plate. Mode of operation of such a divider remains unchanged.

Divider 6 can be attached to plate 4. This device is useful when removal of the divider is not required, and offers the following advantages over a compartmentalized plate. First, medium does not have to be poured separately into each compartment, because it will flow under the divider (which is not making contact with bottom of plate 4 other than via "legs" 10), and will distribute over the entire tray when poured into one of the compartments. Second, stacking and handling of individual plates is avoided. Third, means of collecting beads are provided.

What is claimed is:

1. A method for growing clones of microorganisms, comprising:

a. providing a sterilized open-topped plate, which comprises
      a layer of solid growth medium having a substantially flat surface and a predetermined thickness, and
      a sterilized divider comprising a set of connected vertical walls, said divider inserted into a predetermined portion of said thickness and extending to a predetermined height above said flat surface, said divider so configured and made of such material that adhesion of medium to said divider is sufficiently weak to allow said divider to be removed from said layer without disturbing said layer,
      whereby said flat surface is divided into a plurality of individual growth areas, b. adding a suspension of said microorganisms into each of the growth areas, c. spreading said suspension within said growth areas, d. removing said divider from said layer, and e. allowing said microorganisms to form clones of a predetermined size on said flat surface, whereby said flat surface is made accessible to replicators and membranes that fit within said plate to allow replica-plating and membrane lifts to be performed on said open surface as a whole.

2. The method of claim 1, further including the steps of forming said plate, comprising:

a. melting said medium b. pouring said medium into a sterilized open-topped container, whereby said layer is formed c. inserting said divider into said layer, and d. cooling said layer to solidify said layer.

3. The method of claim 1, further including the steps of forming said plate, comprising:

a. inserting said divider into a sterilized open-topped container, b. melting said medium c. pouring said medium into said container, whereby said layer is formed d. cooling said layer to solidify said layer.

4. The method of claim 1, further including the steps of forming said plate, comprising:

a. melting said medium b. pouring said medium into a sterilized open-topped container, whereby said layer is formed c. cooling said layer to solidify said layer, and d. inserting said divider into said layer.

5. The method of claim 1, wherein said step of spreading said suspension comprises:

a. providing sterilized beads of a diameter that is sufficiently small compared to the height of said walls to allow said walls to confine said beads to said growth areas, b. adding said beads to said growth areas, c. agitating said plate sufficiently to cause said beads to move within said growth areas while being prevented from crossing from one of said growth areas to another by said walls, and d. removing said beads, whereby said clones arising from said microorganisms in each of the individual growth areas do not contact each other.

6. The method of claim 1, further including a. the step of placing said beads into said growth areas, prior to said step of addition of said suspension b the step of spreading said suspension within said growth areas, comprising agitating said plate to cause said beads to move within said growth areas, and removing said beads, whereby said microorganisms are sufficiently well distributed within said growth areas to prevent said clones arising from said microorganisms from coming in contact with each other.

7. The method of claim 1, wherein said clones are selected from the group consisting of bacterial colonies, yeast colonies, and phage plaques.

8. A method for growing clones of microorganisms, comprising:

a. providing a sterilized open-topped plate, comprising
a layer of solid growth medium having a substantially flat surface and a predetermined thickness, and
a sterilized divider comprising a set of connected vertical walls, said walls having a smaller vertical extent than said thickness, said walls inserted into a predetermined portion of said thickness and extending to a predetermined height above said flat surface, whereby said flat surface is divided into a plurality of individual growth areas, b. adding a suspension of said microorganisms into each of the growth areas, c. spreading said suspension within said growth areas, d. pushing said divider completely into said layer, whereby the divider does not extend above said layer, and e. allowing said microorganisms to form clones of a predetermined size on said flat surface, whereby said flat surface is made accessible to replica-plators and membranes that fit within said plate to allow replica-plating and membrane lifts to be performed on said flat surface as a whole.

* * * * *